(12) United States Patent
Chaudhari et al.

(10) Patent No.: US 7,288,672 B2
(45) Date of Patent: Oct. 30, 2007

(54) PROCESS FOR PREPARATION OF ESTERS OF HYDROXY TIGLIC ALDEHYDES

(75) Inventors: Raghunath Vitthal Chaudhari, Maharashtra (IN); Rashmi Chansarkar, Maharashtra (IN); Kausik Mukhopadhyay, Maharashtra (IN); Ashutosh Anant Kelkar, Maharashtra (IN)

(73) Assignee: Council of Scientific & Industriual Research, New Delhi (IN)

( * ) Notice: Subject to any disclaimer, the term of this patent is extended or adjusted under 35 U.S.C. 154(b) by 398 days.

(21) Appl. No.: 10/813,696

(22) Filed: Mar. 29, 2004

(65) Prior Publication Data
US 2005/0215814 A1  Sep. 29, 2005

(51) Int. Cl.
*C07C 67/36* (2006.01)
(52) U.S. Cl. .................................... 560/232
(58) Field of Classification Search ..................... None
See application file for complete search history.

(56) References Cited

U.S. PATENT DOCUMENTS 4,124,619 A * 11/1978 Fitton et al. ................ 554/111

OTHER PUBLICATIONS

El Ali et al, Abtracts of Papers 224th ACS National Meeting, Boston, MA, Hydroformylation and Acetalization of Styrene Derivatives Catalyzed by Rh(III)-phosphite and Rh(III) Supported on MCM-41-phosphite Systems,2002.*

* cited by examiner

*Primary Examiner*—Paul A. Zucker
(74) *Attorney, Agent, or Firm*—Morgan & Finnegan, L.L.P.

(57) ABSTRACT

The present invention relates to a process for the preparation of esters of hydroxy tiglic aldehydes which are the key intermediates for Vitamin-A acetate synthesis and various perfumistic products, said process relates to the hydroformylation of biscarboxylic esters of but-2-ene-1,4-diol, followed by deacetoxylation of its hydroformylation compound, in the presence of heterogeneous catalyst having rhodium complex entrapped, anchored or teethered on the acidic support, said acidic support causes deacetoxylation in the reaction mixture immediately after hydroformylation, to give 100% selectivity to the carboxylic esters of hydroxyl tiglic aldehydes in a single step.

22 Claims, 3 Drawing Sheets

(R can be an alkyl or aryl group)

$HRh(CO)L_3$,
FIGURE 4
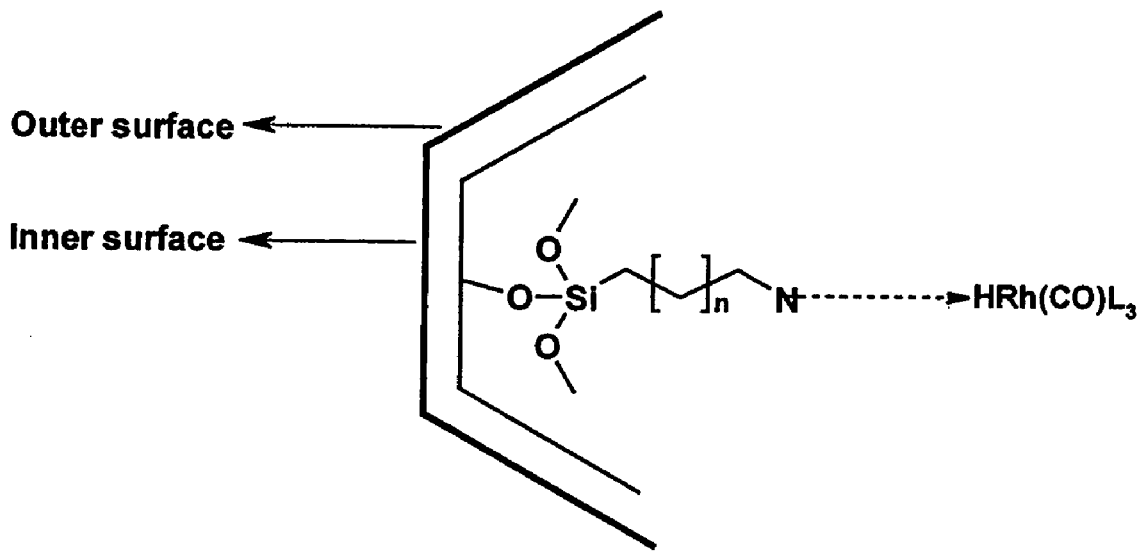
FIGURE 5
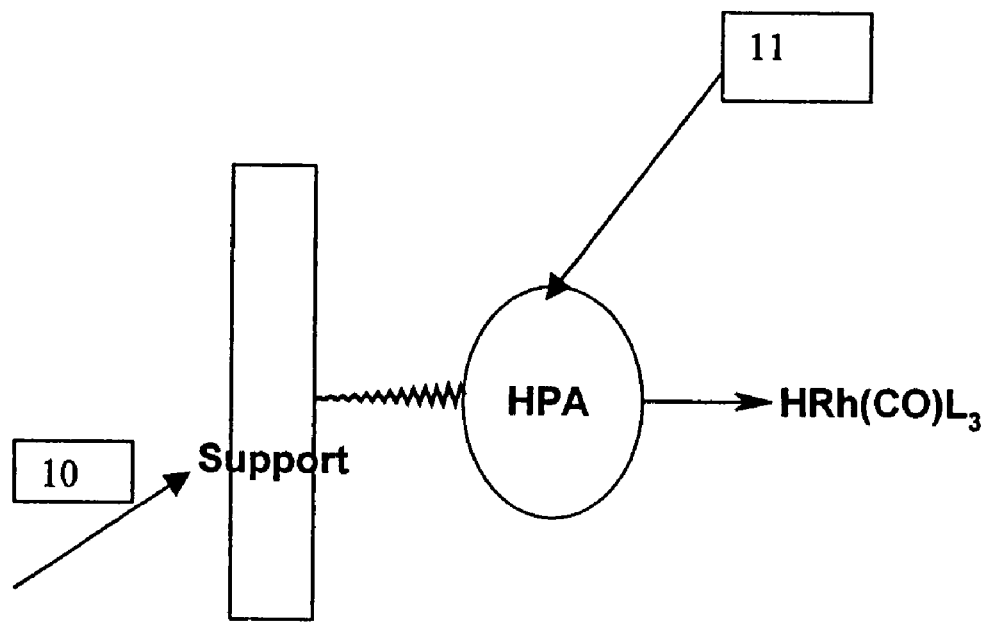
FIGURE 6

PROCESS FOR PREPARATION OF ESTERS OF HYDROXY TIGLIC ALDEHYDES

FIELD OF INVENTION

The present invention relates to an improved process for the preparation of esters of hydroxy tiglic aldehydes which are the key intermediates for Vitamin-A acetate synthesis and various perfumistic products. More Particularly, the process relates to the hydroformylation of biscarboxylic esters of but-2-ene-1,4-diol having the general formula 1, wherein R can be alkyl or aryl, followed by deacetoxylation of its hydroformylation compound, having the general formula 2, in a single step, to give esters of hydroxy tiglic aldehydes, having the general formula 3.

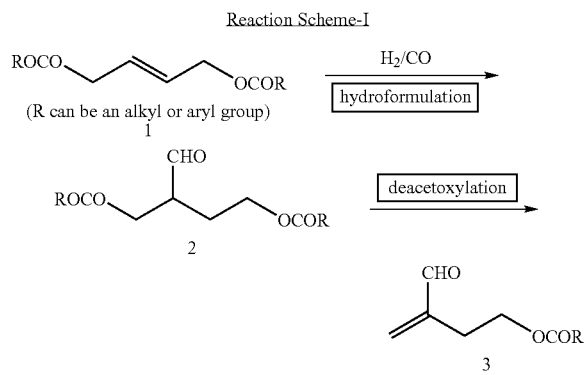

BACKGROUND AND PRIOR ART DESCRIPTION

The carboxylic esters of γ-hydroxy tiglic aldehydes have attracted strong industrial interest, as they are known intermediates for vitamin-A and various perfumistic products. Various methods have been described in the prior art for the preparation of these esters. U.S. Pat. No. 3,760,004 by Freyschlag et al, discloses the preparation of these esters by halogenating a member of the group consisting of 2-formyl-2-hydroxybutene-3 and a di-lower alkyl acetal and a lower fatty acid acylate, with a halogenating agent selected from the group consisting of thionyl chloride, thionyl bromide and phosgene in the presence of a tertiary amine. This conventional process for the synthesis of the carboxylic esters of γ-hydroxy tiglic aldehyde suffers from the drawback of using harmful gases like phosgene, thionyl chloride or thionyl bromide. Bis-monocarboxylicacid esters of 3-formylbutane-1,2-diol have also been used as starting materials for the synthesis of the esters of γ-hydroxy tiglic aldehydes as disclosed in U.S. Pat. No. 3,732,287 by Himmmele et al. This patent describes a process where Bis-monocarboxylicacid esters of 3-formylbutanediol-1,2 are hydroformylated in the presence of carbonyl complex of rhodium at elevated temperatures and super atmospheric pressures. The pressure requirements are from 300-1000 atmospheres. The use of very high temperatures and pressures involves the use of expensive equipment and costly handling procedures to get the desired product. The use of such high pressures mitigates against the commercialization of this process. U.S. Pat. No. 4,124,619 by Fitton et al, discloses another method of synthesis, via the hydroformylation route, using biscarboxylic acid esters of but-2-ene-1,4-diols as the starting material to give carboxylic esters of γ-hydroxy tiglic aldehydes. In this patent biscarboxylic acid esters of but-2-ene-1,4-diols are converted to the compound of the formula 2 by treating with a mixture of carbon monoxide and hydrogen in the presence of a Rhodium catalyst. In a separate step the compound 2 is converted to compound 3 by pyrolysis in the presence of a strong organic or inorganic acid catalyst at a temperature of from 70° C. to 250° C. at atmospheric pressure or under vaccum of 1 mm Hg to 700 mm Hg. This patent describes the hydroformylation route using the homogeneous Rhodium catalyst system. The major disadvantage of this route is a great difficulty in separating the catalyst from the reaction mixture. Distillation has to be done to separate the products from the catalyst system. The catalyst is not stable after distillation at higher temperatures. And then deacetoxylation is done as a separate step, which requires the presence of strong acid catalysts or elevated temperatures.

The conventional processes for the synthesis of carboxylic esters of γ-hydroxy tiglic aldehydes suffer from many drawbacks. The earliest procedures by conventional routes require the use of harmful halogenating gases (U.S. Pat. No. 3,760,004). The later processes using the oxo reaction proved to be non-economical because of the very high-pressure requirements (U.S. Pat. No. 3,732,287). Another process using the hydroformylation route at comparatively lower pressure conditions uses the Rhodium catalyst system in the homogeneous reaction conditions, and so there is a difficulty in separating the catalyst from the reaction mixture and there is a loss in the amount of product upon distillation (U.S. Pat. No. 4,124,619). And deacetoxylation to get the required carboxylic esters of γ-hydroxy tiglic aldehydes is a two-step process.

There is a commercial interest in carboxylic esters of γ-hydroxy tiglic aldehydes, as they are well known intermediates for vitamin-A and various perfumery applications. An increasing academic as well as industrial attention has been paid towards research in developing new methods for the higher selectivity of carboxylic esters of γ-hydroxy tiglic aldehydes and easy catalyst separation from the reaction mixture. In view of the advantages and the features of the present invention, this improved process, would be a significant advance in the current state of art related to the synthesis of carboxylic esters of γ-hydroxy tiglic aldehydes by the hydroformylation route, having easy catalyst separation and a 100% selectivity towards carboxylic esters of γ-hydroxy tiglic aldehydes in a single step.

OBJECTS OF THE INVENTION

The main objective of the present invention is to provide a catalytic route for the preparation of carboxylic esters of γ-hydroxy tiglic aldehydes, free of the drawbacks discussed above.

Another objective of the present invention is to provide provides a single step process for the preparation of carboxylic esters of γ-hydroxy tiglic aldehydes, by reacting Biscarboxylic esters of but-2-ene-1,4-diols having the general formula 1, where R can be alkyl or aryl, hydrogen and carbon monoxide, the process being carried out in the presence of a heterogeneous catalyst and preferably a liquid diluent for the preparation of 3 with 100% selectivity and easy catalyst separation.

Yet another objective of the present invention is to provide a route for the preparation of 3 which require the use of the starting material in very stable form, easy to handle and economical.

SUMMARY OF THE INVENTION

To attain the above described objects, the present invention provides a simple, cost effective and reliable process for the preparation of esters of hydroxy tiglic aldehydes which are the key intermediates for Vitamin-A acetate synthesis and various perfumistic products.

DETAILED DESCRIPTION OF THE INVENTION

Accordingly, the present invention provides a process for the preparation of esters of hydroxy tiglic aldehydes which are the key intermediates for Vitamin-A acetate synthesis and various perfumistic products.

In an embodiment of the present invention relates to an improved process for preparing the esters of γ-hydroxy tiglic aldehydes, said process comprising; hydroformylation of biscarboxylic esters of but-2-ene-1,4-diol having the general formula 1, where R is $C_1$ to $C_{12}$ alkyl or aryl, followed by deacetoxylation of its hydroformylation compound, having the general formula 2, in the presence of organo metallic heterogeneous catalyst, hydrogen, carbon monoxide at elevated temperatures and in presence of solvent to obtain desired Esters of hydroxy tiglic aldehydes having the general formula 3.

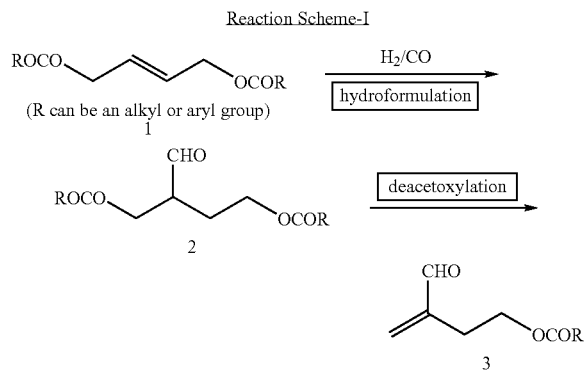

Reaction Scheme-I

In another embodiment of the present invention wherein the biscarboxylic esters of but-2-ene-1,4-diols are selected from the group comprising butene-2-diol-1,4-diacetate, butene-2-diol-1,4-diformate, butene-2-diol-1,4-dipropionate, butene-2-diol-1,4-dibutyrate, butene-2-diol-1,4-diisobutyrate, butene-2-diol-1,4-dipalmitate, butene-2-diol-1,4-dibenzoate.

In yet another embodiment of the present invention wherein the organo metallic heterogeneous catalysts are selected from the group comprising Rhodium complex anchored, tethered or entrapped on a heterogeneous support.

In still another embodiment of the present invention wherein the Rhodium metal complex having a general formula HRh(CO)L$_3$, Wherein:

L represents a ligand, characterized by the presence of at least one heteroatom selected from the group containing Nitrogen, Phosphorus, oxygen or a combination thereof.

In a further embodiment of the present invention wherein ligand used are monodentate or multidentate.

In a further embodiment of the present invention wherein the monodentate ligands are selected from the group comprising trialkyl, triaryl or arylalkyl phosphines.

In one more embodiment of the present invention wherein the multidentate are selected from the group comprising diphenyl phosphino, methane, diphenyl phosphino ethane, diphenyl phosphino propane, diphenyl phosphino butane, 2-diphenylphosphino-[N-(2-diphenylphosphino)oxy]ethyl]-Nmethyl]-benzamine.

In one another embodiment of the present invention wherein the organo metallic Rhodium complex HRh(CO)L$_3$, is anchored to the internal surface of MCM-41 or MCM-48 in presence of an anchoring agent.

In another embodiment of the present invention wherein the anchoring agent used are a functionalized-alkyl-substituted (Z—[CH$_2$]$_n$—) silane containing at least one alkoxy group (—OR) attached to the silicon atom, having a general formula of Z—(CH$_2$)$_n$—Si(OR)$_m$H$_{3-m}$ wherein Z is a functional group as —NH$_2$, —SH, vinyl, allyl etc., "n" may have integral values between 2 and 6, "m" may have integral values between 1 and 3 and represented

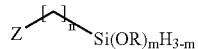

In yet another embodiment of the present invention wherein the organo metallic complex HRh(CO)L$_3$, is tethered on the surface of the heterogeneous support by means of an inorganic heteropolyacid (HPA).

In yet another embodiment of the present invention wherein the tethering moiety used. for anchoring the transition metal complex to the solid matrix are an inorganic heteropoly acid, having the primary Keggin ion structure.

In still another embodiment of the present invention wherein the HPA used are phosphotungstic acid and phosphomolybdic acid.

In yet another embodiment of the present invention wherein the organometallic complex HRh(CO)L$_3$, is entrapped inside the microporous hosts.

In another embodiment of the present invention wherein the solvents used are conventional inert organic solvent or hydrocarbon solvents.

In yet another embodiment of the present invention wherein hydrocarbon solvent used are selected from the group comprising benzene, xylene, toluene, cyclohexane, isooctane, hexane, ethers such as diethyl ether, tetrahydrofuran or dioxane, esters such as ethyl acetate or methyl propionate: or alcohols such as methanol or n-butane.

In another embodiment of the present invention wherein the process is carried out in the presence of carbon monoxide and hydrogen in a volumetric ratio in the range of 1:2 to 2:1, In still another embodiment of the present invention wherein the process is carried out in presence of carbon monoxide and hydrogen in a volumetric ratio of 1:1.

In yet another embodiment of the present invention wherein the reaction is carried out at a pressure in the range 10-1000 atmospheres.

In yet another embodiment of the present invention wherein the reaction is carried out at a pressure in the range 10-140 atmospheres.

In yet another embodiment of the present invention wherein the process is carried out in the range of 50-120° C.

BRIEF DESCRIPTION OF THE FIGURES

FIG. 4 represents a heterogeneous catalyst containing a Rhodium metal complex

FIG. 5 shows the organo metallic complex $HRh(CO)L_3$, 4 is prepared according to the literature procedure[1]. Here the complex is anchored to the internal surface of the solid matrix by an anchoring agent, the agent for fictionalization i.e. the chemical agent used for anchoring the transition metal complexes to the pretreated matrices may be a functionalized-alkyl-substituted $(Z-[CH_2]_n-)$ silane containing at least one alkoxy group $(-OR)$ attached to the silicon atom, having a general formula of $Z-(CH_2)_n-Si(OR)_m H_{3-m}$ wherein Z is a functional group as $-NH_2$, $-SH$, vinyl, allyl etc., "n" may have integral values between 2 and 6, "m" may have integral values between 1 and 3. It may be represented as shown in the illustration as 8.

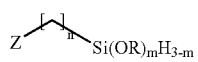

8

FIG. 6 depicts the organometallic complex $HRh(CO)L_3$, 4 is prepared according to the literature procedure[2]. The complex is tethered on the surface of the heterogeneous support by means of an inorganic heteropolyacid (HPA). The tethering moiety i.e. the chemical agent used for anchoring the transition metal complexes to the solid matrix may be an inorganic heteropoly acid, having the primary Keggin ion structure. The heteropolyacids used may be phosphotungstic acid, phosphomolybdic acid etc.

Figure 1:
FIG. 1 shows structural formula of but-2-ene-1,4-diol-esters.
Figure 2:
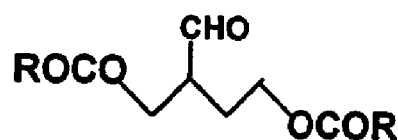
FIG. 2 shows structural formula of hydroformylation compound.
Figure 3:
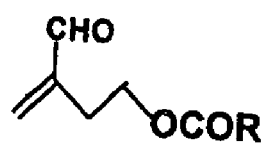
FIG. 3 shows the structural formula of esters of hydroxy tiglic aldehydes.
Figure 7:
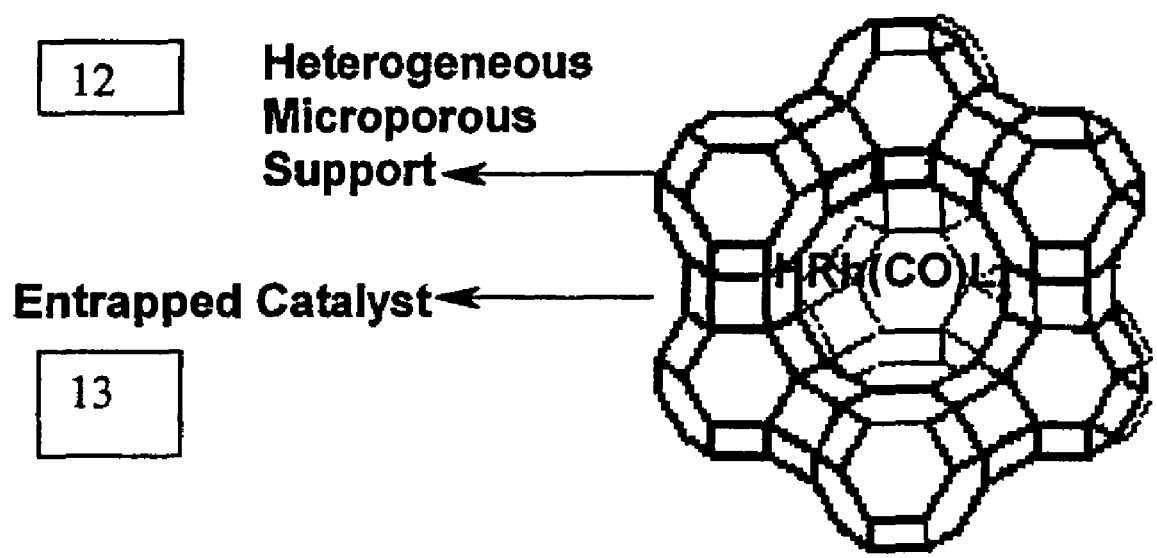

FIG. 7 represents the organometallic complex $HRh(CO)L_3$, 4 is entrapped inside the microporous hosts.

The catalysts thus prepared are solid, robust and heterogeneous and hence, separable from the reaction mixture by simple filtration techniques. The acidity of the support makes them very special to get a complete selectivity for the required compounds of the formula 3.

In another embodiment, the process according to this invention is preferably carried out in the presence of a solvent. A wide variety of liquids that remain liquid under the reaction conditions can serve as solvents. Any conventional inert organic solvent can be utilized in carrying out this reaction. Among the preferred solvents are hydrocarbon solvents such as benzene, xylene, toluene, cyclohexane, isooctane, hexane: ethers such as diethyl ether, tetrahydrofuran or dioxane, esters such as ethyl acetate or methyl propionate, or alcohols such as methanol or n-butane. There is no limit on the amount of the solvent used and it may be decided on other process related issues like stirrability, solubility of reactants, process economics etc.

It is obviously preferred that the compounds used, according to the present invention, are stable and free from any other functionality which may react under the reaction conditions or retard the formation of desired product.

In another embodiment, the process of invention is carried out in the presence of a heterogeneous catalyst containing a Rhodium metal complex represented by the formula $HRh(CO)L_3$ (4), either anchored, tethered or entrapped on a heterogeneous support. L in 4 represents a ligand, characterized by the presence of at least one heteroatom selected from the group containing Nitrogen, Phosphorus, oxygen or a combination thereof. The ligand can be monodentate or bidentate or multidentate or a combination of both. The suitable examples of monodentate ligands include trialkyl, triaryl or arylalkyl phosphines eg. tri-t-butylphosphine, triphenyl phosphine, chlorodiphenyl phosphine. Multidentate ligands include diphenyl phosphino methane, diphenyl phosphino ethane, diphenyl phosphino propane, diphenyl phosphino butane, 2-diphenylphosphino-[N-(2-diphenylphosphino)oxy]ethyl]]-Nmethyl]-benzamine.

The support for the heterogeneous catalysts of the present invention can be any suitable solid matrix with acidic properties, intended for use with the insoluble catalysts including, but not limited to micro porous and mesoporous materials that may be selected from Zeolite Y, Zeolite, ZSM-5 etc. (microporous), or MCM-41, MCM-48 etc. (mesoporous) or Silica respectively. The support materials were designed in such a way that they may be purely siliceous or aluminated (containing aluminium in the matrix framework). Purely Siliceous supports or aluminosilicates impart the required acidic properties to the support, which are required for the deacetoxylation step. The support preferably has certain mechanical stabilities so that it remains sturdy in the machinery during catalytic reactions, and does not break into particles when reactants flow through it. More particularly it relates to the preparation of immobilized transition metal complex catalysts having a general representation as in either formula 5, 6 or 7.

In another embodiment, the carbon monoxide and hydrogen are generally used in a volumetric ratio of 1:2 to 2:1, particularly about 1:1. The reaction is carried out at pressures of from 10-1000 atmospheres, preferably in the range of 13-136 atmospheres.

In another embodiment, the temperature in the range of 50-120° C. can be used in carrying out this reaction.

The embodiments and examples described here to illustrate the catalyst activity and the process by no way limit the scope of the present invention and variety of similar type of substrates, that react in presence of said catalyst and conditions to give 3 can be used.

The present invention is described in more details in reference to the following examples.

EXAMPLE 1

A solution of 1,4-diacetoxy-2-butene (0.5 g) and HRh (CO)(PPh$_3$)$_3$-entrapped in Zeolite-Y (0.05 g) in toluene (25 ml) was heated in an autoclave at 75° C., under 1000 psig of synthesis gas (50% by volume H$_2$ and 50% by volume CO gas). The reaction was monitored for gas absorption. After the theoretical amount of gas absorption (44 psig) took place and consequently there was no further gas uptake, the reaction was stopped and then the autoclave was cooled to room temperature. The solid catalyst was recovered by decantation of the reaction mixture. The reaction mixture was analyzed by HP 6890 gas chromatograph to give pure 2-Formyl-4-acetoxybutene (99.9% yield and 100% selectivity to 2-Formyl-4-acetoxybutene). Later toluene was removed from the reaction mixture by distillation to get the pure fraction of 2-Formyl-4-acetoxybutene (b.p. 78-79° C./5 mm Hg). The recovered catalyst was recycled six times. It was found that there was no losses in activity upon each recycle. ICP analysis also showed no leaching of the rhodium catalyst.

EXAMPLE 2

A solution of 1,4-diacetoxy-2-butene (0.5 g) and HRh(CO)(PPh$_3$)$_3$-tethered on Zeolite-Y (0.05 g) in toluene (25 ml) was heated in an autoclave at 85° C., under 1200 psig of synthesis gas (50% by volume H$_2$ and 50% by volume CO gas). The reaction was monitored for gas absorption. After the theoretical amount of gas absorption (44 psig) took place and consequently there was no further gas uptake, the reaction was stopped and then the autoclave was cooled to room temperature. The solid catalyst was recovered by decantation of the reaction mixture. The reaction mixture was analyzed by HP 6890 gas chromatograph to give pure 2-Formyl-4-acetoxybutene (99.9% yield and 100% selectivity to 2-Formyl-4-acetoxybutene). Later toluene was removed from the reaction mixture by distillation to get the pure fraction of 2-Formyl-4-acetoxybutene (b.p. 78-79° C./5 mm Hg). The recovered catalyst was recycled five times. It was found that there was no loss in activity upon each recycle. ICP analysis also showed no leaching of the rhodium catalyst.

EXAMPLE 3

A solution of 1,4-diacetoxy-2-butene (0.5 g) and HRh(CO)(PPh$_3$)$_3$-anchored in MCM-41 (0.05 g) in toluene (25 ml) was heated in an autoclave at 75° C., under 1000 psig of synthesis gas (50% by volume H$_2$ and 50% by volume CO gas). The reaction was monitored for gas absorption. After the theoretical amount of gas absorption (44 psig) took place and consequently there was no further gas uptake, the reaction was stopped and then the autoclave was cooled to room temperature. The solid catalyst was recovered by decantation of the reaction mixture. The reaction mixture was analyzed by HP 6890 gas chromatograph to give pure 2-Formyl-4-acetoxybutene (99.9% yield and 100% selectivity to 2-Formyl-4-acetoxybutene). Later toluene was removed from the reaction mixture by distillation to get the pure fraction of 2-Formyl-4-acetoxybutene (b.p. 78-79° C./5 mm Hg). The recovered catalyst was recycled five times. It was found that there was no loss in activity upon each recycle. ICP analysis also showed no leaching of the rhodium catalyst.

EXAMPLE 4

A solution of 1,4-diacetoxy-2-butene (0.5 g) and HRh(CO)(PPh$_3$)$_3$-anchored in MCM-48 (0.05 g) in toluene (25 ml) was heated in an autoclave at 75° C., under 800 psig of synthesis gas (50% by volume H$_2$ and 50% by volume CO gas). The reaction was monitored for gas absorption. After the theoretical amount of gas absorption (44 psig) took place and consequently there was no further gas uptake, the reaction was stopped and then the autoclave was cooled to room temperature. The solid catalyst was recovered by decantation of the reaction mixture. The reaction mixture was analyzed by HP 6890 gas chromatograph to give pure 2-Formyl-4-acetoxybutene (99.9% yield and 100% selectivity to 2-Formyl-4-acetoxybutene). Later toluene was removed from the reaction mixture by distillation to get the pure fraction of 2-Formyl-4-acetoxybutene (b.p. 78-79° C./5 mm Hg). The recovered catalyst was recycled five times. It was found that there was no loss in activity upon each recycle. ICP analysis also showed no leaching of the rhodium catalyst.

EXAMPLE 5

A solution of 1,4-diacetoxy-2-butene (0.5 g) and HRh(CO)(PPh$_3$)$_3$-tethered on silica (0.05 g) in toluene (25 ml) was heated in an autoclave at 75° C., under 900 psig of synthesis gas (50% by volume H$_2$ and 50% by volume CO gas). The reaction was monitored for gas absorption. After the theoretical amount of gas absorption (44 psig) took place and consequently there was no further gas uptake, the reaction was stopped and then the autoclave was cooled to room temperature. The solid catalyst was recovered by decantation of the reaction mixture. The reaction mixture was analyzed by HP 6890 gas chromatograph to give pure 2-Formyl-4-acetoxybutene (99.9% yield and 100% selectivity to 2-Formyl-4-acetoxybutene). Later toluene was removed from the reaction mixture by distillation to get the pure fraction of 2-Formyl-4-acetoxybutene (b.p. 78-79° C./5 mm Hg). The recovered catalyst was recycled five times. It was found that there was no loss in activity upon each recycle. ICP analysis also showed no leaching of the rhodium catalyst.

EXAMPLE 6

A solution of 1,4-diacetoxy-2-butene (0.5 g) and HRh(CO)(PPh$_3$)$_3$ tethered on zeolite-β (0.05 g) in toluene (25 ml) was heated in an autoclave at 80° C., under 1000 psig of synthesis gas (50% by volume H$_2$ and 50% by volume CO gas). The reaction was monitored for gas absorption. After the theoretical amount of gas absorption (44 psig) took place and consequently there was no further gas uptake, the reaction was stopped and then the autoclave was cooled to room temperature. The solid catalyst was recovered by decantation of the reaction mixture. The reaction mixture was analyzed by HP 6890 gas chromatograph to give pure 2-Formyl-4-acetoxybutene (99.9% yield and 100% selectivity to 2-Formyl-4-acetoxybutene). Later toluene was removed from the reaction mixture by distillation to get the pure fraction of 2-Formyl-4-acetoxybutene (b.p. 78-79° C./5 mm Hg). The recovered catalyst was recycled five times. It was found that there was no losses in activity upon each recycle. ICP analysis also showed no leaching of the rhodium catalyst.

EXAMPLE 7

A solution of 1,4-diacetoxy-2-butene (0.5 g) and HRh(CO)(PPh$_3$)$_3$-tethered on alumina (0.05 g) in toluene (25 ml) was heated in an autoclave at 70° C., under 1000 psig of synthesis gas (50% by volume H$_2$ and 50% by volume CO gas). The reaction was monitored for gas absorption. After the theoretical amount of gas absorption (44 psig) took place and consequently there was no further gas uptake, the reaction was stopped and then the autoclave was cooled to room temperature. The solid catalyst was recovered by decantation of the reaction mixture. The reaction mixture was analyzed by HP 6890 gas chromatograph to give 30% Diacetoxy-2-formyl-butane and 70% 2-Formyl-4-acetoxybutene. The recovered catalyst was recycled five times. It was found that there was no loss in activity upon each recycle. ICP analysis also showed no leaching of the rhodium catalyst tethered on alumina.

What is claimed is:

1. An improved process for preparing the esters of γ-hydroxy tiglic aldehydes, said process comprising; hydroformylation of biscarboxylic esters of but-2-ene-1,4-diol having the general formula 1, wherein R is C$_1$ to C$_{12}$ alkyl or aryl, followed by deacetoxylation of its hydroformylation compound, having the general formula 2, in the presence of organo metallic heterogeneous catalyst, hydrogen, carbon monoxide at elevated temperatures and in presence of solvent to obtain desired Esters of hydroxy tiglic aldehydes having the general formula

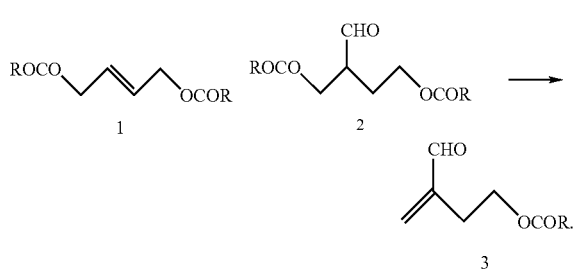

2. The process as claimed in claim 1, wherein the biscarboxylic esters of but-2-ene-1,4-diols are butene-2-diol-1,4-diacetate, butene-2-diol-1,4-diformate, butene-2-diol-1,4-dipropionate, butene-2-diol-1,4-dibutyrate, butene-2-diol-1,4-diisobutyrate, butene-2-diol-1,4-dipalmitate, or butene-2-diol-1,4-dibenzoate.

3. The process as claimed in claim 1, wherein the organo metallic heterogeneous catalyst is a Rhodium complex anchored, tethered or entrapped on a heterogeneous support.

4. The process as claimed in claim 3, wherein the Rhodium metal complex has a general formula $HRh(CO)L_3$, Wherein:

L represents a ligand having at least one heteroatom of nitrogen, phosphorus, oxygen or a combination thereof.

5. The process as claimed in claim 4, wherein the ligand is monodentate or multidentate.

6. The process as claimed in claim 5, wherein the monodentate ligand is a trialkyl, a triaryl or an arylalkyl phosphine.

7. The process as claimed in claim 5, wherein the multidentate ligand is diphenyl phosphino methane, diphenyl phosphino ethane, diphenyl phosphino propane, diphenyl phosphino butane, or 2-diphenylphosphino-[N-(2-diphenylphosphino)oxy]ethyl]-N-methyl]-benzamine.

8. The process as claimed in claim 3, wherein the organo metallic Rhodium complex $HRh(CO)L_3$, is anchored to the internal surface of MCM-41 or MCM-48 in presence of an anchoring agent.

9. The process as claimed in claim 8, wherein the anchoring agent used is a functionalized-alkyl-substituted ($Z-[CH_2]_n-$) silane containing at least one alkoxy group (—OR) attached to the silicon atom, having a general formula of $Z-(CH_2)_n-Si(OR)_mH_{3-m}$ wherein Z is a functional group $-NH_2$, $-SH$, vinyl, or allyl, "n" has an integral value between 2 and 6, "m" has an integral value between 1 and 3 and represented by

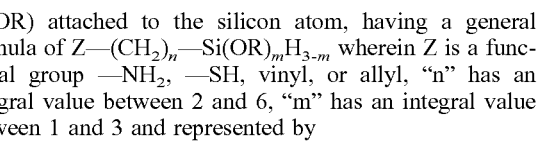

10. The process as claimed in claim 3, wherein the organo metallic complex $HRh(CO)L_3$, is tethered on the surface of the heterogeneous support by means of an inorganic heteropolyacid (HPA).

11. The process as claimed in claim 10, wherein the tethering moiety used for anchoring the transition metal complex to the solid matrix is an inorganic heteropoly acid, having the primary Keggin ion structure.

12. The process as claimed in claim 10, wherein the HPA used is phosphotungstic acid or phosphomolybdic acid.

13. The process as claimed in claim 3, wherein the organometallic complex $HRh(CO)L_3$, is entrapped inside the microporous hosts.

14. The process as claimed in claim 1, wherein the solvents used are conventional inert organic solvent or hydrocarbon solvents.

15. The process as claimed in claim 1, wherein solvent used is benzene, xylene, toluene, cyclohexane, isooctane, hexane, diethyl ether, tetrahydrofuran, dioxane, ethyl acetate, methyl propionate, methanol or n-butane.

16. The process as claimed in claim 1, wherein the process is carried out in the presence of carbon monoxide and hydrogen in a volumetric ratio in the range of 1:2 to 2:1.

17. The process as claimed in claim 16, wherein the process is carried out in the presence of carbon monoxide and hydrogen in a volumetric ratio of 1:1.

18. The process as claimed in claim 1, wherein the reaction is carried out at a pressure in the range 10-1000 atmospheres.

19. The process as claimed in claim 18, wherein the reaction is carried out at a pressure in the range 10-140 atmospheres.

20. The process as claimed in claim 1, wherein the process is carried out in the range of 50-120° C.

21. The process as claimed in claim 1, wherein thus obtained esters of hydroxy tiglic aldehydes have a selectivity of about 100%.

22. The process as claimed in claim 1, wherein the solvent used is a hydrocarbon, an ether, an ester or an alcohol.

* * * * *

UNITED STATES PATENT AND TRADEMARK OFFICE
CERTIFICATE OF CORRECTION

| | |
|---|---|
| PATENT NO. | : 7,288,672 B2 |
| APPLICATION NO. | : 10/813696 |
| DATED | : October 30, 2007 |
| INVENTOR(S) | : Raghunath Vitthal Chaudhari et al. |

Page 1 of 1

It is certified that error appears in the above-identified patent and that said Letters Patent is hereby corrected as shown below:

On the Title Page,

Item (54) – TITLE; insert --IMPROVED-- before "PROCESS FOR PREPARATION OF ESTERS OF HYDROXY TIGLIC ALDEHYDES."

In Claim 1, line 10, (Col. 9, line 6), after "having the general formula" insert --3--.

In Claim 10, lines 3-4 (Col. 10, lines 14-15) separate the term "heteropolyacid" by adding a space between "heteropoly" and "acid".

In Claim 18, line 2 (Col. 10, line 39) after "in the range" insert --of--.

In Claim 19, line 2 (Col. 10, line 42) after "in the range" insert --of--.

Signed and Sealed this

Fifteenth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,288,672 B2 Page 1 of 1
APPLICATION NO. : 10/813696
DATED : October 30, 2007
INVENTOR(S) : Raghunath Vitthal Chaudhari et al.

It is certified that error appears in the above-identified patent and that said Letters Patent is hereby corrected as shown below:

Title Page,
Item [54], Title, the word "IMPROVED" (as inserted by Certificate of Correction issued April 15, 2008) should be deleted and title is to reinstated to read --PROCESS FOR PREPARATION OF ESTERS OF HYDROXY TIGLIC ALDEHYDES--.

Signed and Sealed this

Sixth Day of May, 2008

JON W. DUDAS
*Director of the United States Patent and Trademark Office*